United States Patent
Gruber et al.

(10) Patent No.: US 7,264,026 B2
(45) Date of Patent: Sep. 4, 2007

(54) REFILL AND STORAGE HOLDER FOR PERSONAL CARE APPLIANCE

(75) Inventors: Paul Gruber, Bodensdorf (AT); Rembert Fertner, Klagenfurt (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/239,269

(22) PCT Filed: Feb. 11, 2002

(86) PCT No.: PCT/IB02/00400

§ 371 (c)(1),
(2), (4) Date: Sep. 20, 2002

(87) PCT Pub. No.: WO02/064328

PCT Pub. Date: Aug. 22, 2002

(65) Prior Publication Data

US 2003/0037447 A1 Feb. 27, 2003

(30) Foreign Application Priority Data

Feb. 12, 2001 (EP) .................................. 01200508

(51) Int. Cl.
 B65B 1/04 (2006.01)
 B65B 3/04 (2006.01)
 B67C 3/02 (2006.01)
(52) U.S. Cl. .................. 141/113; 141/18; 141/94; 141/95; 141/198; 141/347
(58) Field of Classification Search ............ 141/2, 141/18, 94, 95, 100, 102, 105, 113, 192, 198, 141/311 R, 346, 347; 15/22.1; 433/84, 433/87, 89
See application file for complete search history.

(56) References Cited

U.S. PATENT DOCUMENTS

| | | | |
|---|---|---|---|
| 4,877,065 A * | 10/1989 | Lamboy et al. ............... 141/18 |
| 5,150,492 A | 9/1992 | Suroff ....................... 15/22.1 |
| 5,301,381 A | 4/1994 | Klupt ........................ 15/22.1 |
| 6,599,126 B1 * | 7/2003 | Sale et al. .................. 433/216 |

FOREIGN PATENT DOCUMENTS

| EP | 0123765 A1 | 7/1984 |
|---|---|---|
| WO | WO9404106 | 3/1994 |
| WO | WO0041645 | 7/2000 |

* cited by examiner

Primary Examiner—Timothy L. Maust
(74) Attorney, Agent, or Firm—Adam L. Stroud

(57) ABSTRACT

A personal care system (1) comprising a personal care appliance (2) which comprises a body (3), an additive outlet (7), and a first reservoir (8) which is connected with said additive outlet (7) and has a refill inlet (25) for refilling said reservoir (8), a refill unit (16) comprising a refill outlet (35) which can be coupled to the refill inlet (25) of the personal care appliance (2) for refilling the first reservoir (8), which refill unit (16) comprises a second reservoir (26) and means (13) for transporting additive from the second reservoir (26) to the first reservoir (8), when the personal care appliance (2) is coupled to the refill unit (16). The refill unit (16) is provided in a holder (5) for storing the personal care appliance when it is not in use. When the personal care appliance is stored in the same holder in which it is placed to be refilled, both functions are integrated into one holder. The user has to perform a simple operation, placing the personal care appliance in the holder, to realize both storage and refill of the personal care appliance, which enhances the user-friendliness of the system.

11 Claims, 3 Drawing Sheets

REFILL AND STORAGE HOLDER FOR PERSONAL CARE APPLIANCE

Figure 1:
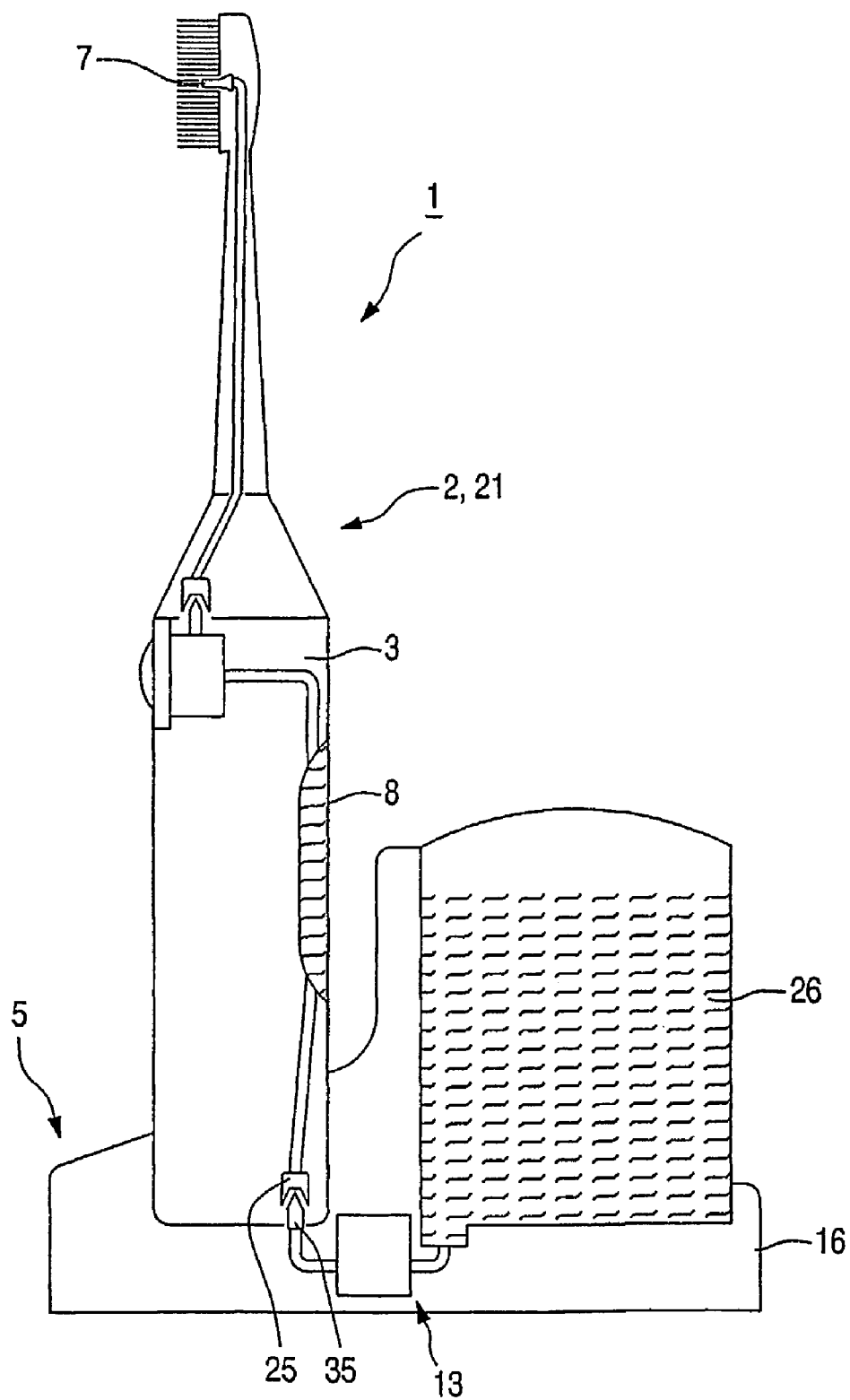

The invention relates to a personal care system comprising a personal care appliance which comprises a body, an additive outlet, and a first reservoir which is connected with said additive outlet and has a refill inlet for refilling said reservoir, a refill unit comprising a refill outlet which can be coupled to the refill inlet of the personal care appliance for refilling the first reservoir, which refill unit comprises a second reservoir and means for transporting additive from the second reservoir to the first reservoir, when the personal care appliance is coupled to the refill unit.

A personal care system of the type defined in the opening paragraph is known from WO 00/41645.

The known system comprises a toothbrush which during operation applies an additive to the teeth of the user via its brush head. During operation the additive is transported from the reservoir in the toothbrush to additive outlets in the brush head. In order to refill the reservoir in the toothbrush after a certain period of time, the refill unit is first placed over the top part of the toothbrush to couple the refill inlet of the toothbrush, here a refill valve, with the refill outlet of the refill unit, here a fill needle. The toothbrush is moved upwardly in the refill unit, to bring the fill needle into contact with the refill valve of the reservoir of the toothbrush, and to activate a transport of an amount of additive from the second reservoir to a further space within the refill unit. The toothbrush then is moved downwardly in the refill unit, to activate a transport of additive from the further space via the fill needle and the refill valve, into the first reservoir of the toothbrush. After that the refill unit is removed from the top part of the toothbrush and the toothbrush is ready for a next use.

A disadvantage of the known system is, that the refilling of the reservoir in the toothbrush is cumbersome for the user. The user has to perform a number of steps in a correct manner and in a correct order to ensure a proper refill of the first reservoir. Furthermore, the system comprises various separate parts, which renders it relatively complex.

It is an object of the invention to provide a personal care system as defined in the opening paragraph, which is more user-friendly.

To achieve this object, a personal care system according to the invention is characterized in that the refill unit is provided in a holder for storing the personal care appliance when it is not in use. After use of the personal care appliance, its reservoir has to be refilled to be ready for the next use of the personal care appliance. Furthermore, the personal care appliance needs to be stored somewhere until the next use. When the refill unit is provided in a holder for storing the personal care appliance when it is not in use, both functions are integrated into one holder. In this manner the period of storage of the personal care appliance may be utilized for refilling the reservoir of the appliance, and the system does not have separate components for each of these functions. This enhances the user-friendliness of the system.

An embodiment of a system according to the invention is characterized in that the personal care appliance is a rechargeable electrical personal care appliance and the holder comprises a charging device for charging the personal care appliance when stored in the holder. The holder is thus also advantageously utilized for recharging of the personal care appliance, next to refilling and storing. In this manner the personal care appliance is ready for use when it is taken out of the holder after a certain period of time, both in respect of its charging level and the contents of its additive supply.

A further embodiment of a system according to the invention is characterized in that the system comprises a sensor for automatic activation of the means for transporting additive on placing of the personal care appliance in the holder, by detecting presence of the personal care appliance in the holder and providing a signal to a processing unit which activates the transporting means in response to said signal. In this manner the refilling of the reservoir of the personal care appliance is started directly when the personal care appliance is placed in the holder. After placing the personal care appliance in the holder, the user does not have to take any additional action to activate the refilling of the reservoir in the personal care appliance by the refill unit, which further enhances the user-friendliness of the system.

An embodiment of a system according to the invention is characterized in that the means for transporting additive comprise a transport channel between the second reservoir and the refill outlet, and the system further comprises a pressure sensor for detecting an overpressure in said transport channel and for providing a signal to the processing unit which de-activates the transporting means in response to said signal. When additive is being transported to the reservoir in the personal care appliance, at a certain moment the reservoir of the personal care appliance will be full. Since the transporting means are then still in action, additive is still being transported from the reservoir in the refill unit via the transport channel to the reservoir in the personal care appliance, and an overpressure will occur in the transport channel. The refilling of the reservoir is automatically stopped by the processing means in response to the signal of the pressure sensor. In this manner a reliable protection against overpressure within the system is offered, which does not need any user intervention.

An embodiment of a system according to the invention is characterized in that the pressure sensor comprises a switch, which co-operates with a flexible membrane which is provided in at least a part of a wall of the transport channel. The overpressure in the transport channel causes the flexible membrane to curve outwardly, and to contact the switch which then sends a signal to the processing unit to de-activate the pump unit. In this construction the switch does not come into contact with the additive within the transport channel. This renders the construction relatively simple and cost-effective from a manufacturing point of view, while it also offers a reliable protection against overpressure occurring within the system.

An embodiment of a system according to the invention is characterized in that a part of the transport channel is formed by the flexible membrane. In this manner the flexible membrane material can be easily integrated into the transport channel, since it can be injection moulded together with the channel.

It is advantageous, when a distance between the switch and the membrane is adjustable for adjusting a value of a pressure at which the flexible membrane contacts the switch. The value of the pressure at which the membrane contacts the switch can be preset in a relatively simple manner during manufacture of the system, in the case where the system comprises one personal care appliance. When the system comprises more than one personal care appliance, it is advantageous when the distance and therewith the pressure at which the membrane curves and contacts the switch can be set depending on the number of personal care appliances which are to be refilled. In this manner the safety of the system regarding the pressure within it is also guaranteed when it comprises more than one personal care appliance.

An embodiment of a system according to the invention is characterized in that the personal care appliance is a toothbrush. The toothbrush can be a non-electrical toothbrush comprising an additive reservoir, or a power toothbrush comprising an additive reservoir.

An embodiment of a system according to the invention is characterized in that the personal care appliance is a shaver.

Figure 2:
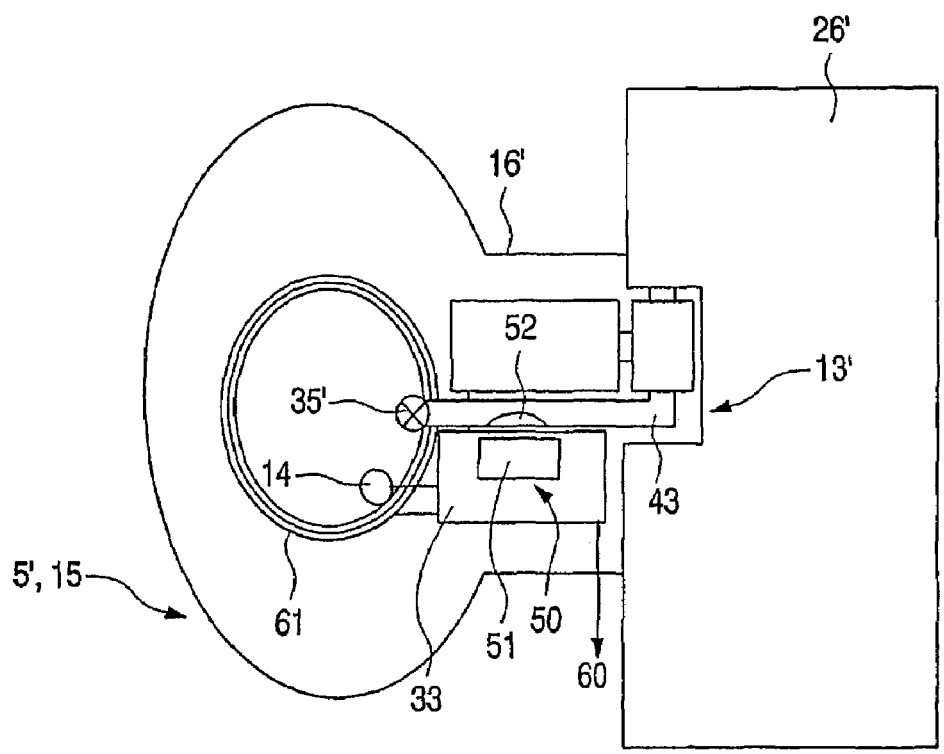
Figure 3A:
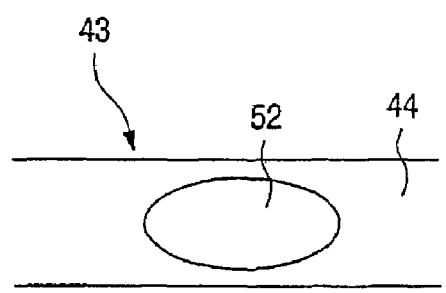
Figure 3B:
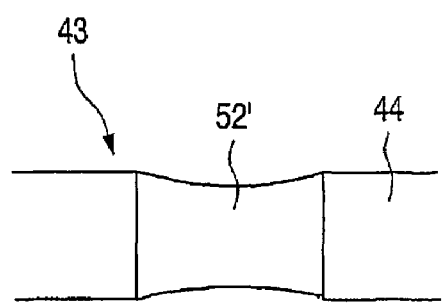
Figure 4:
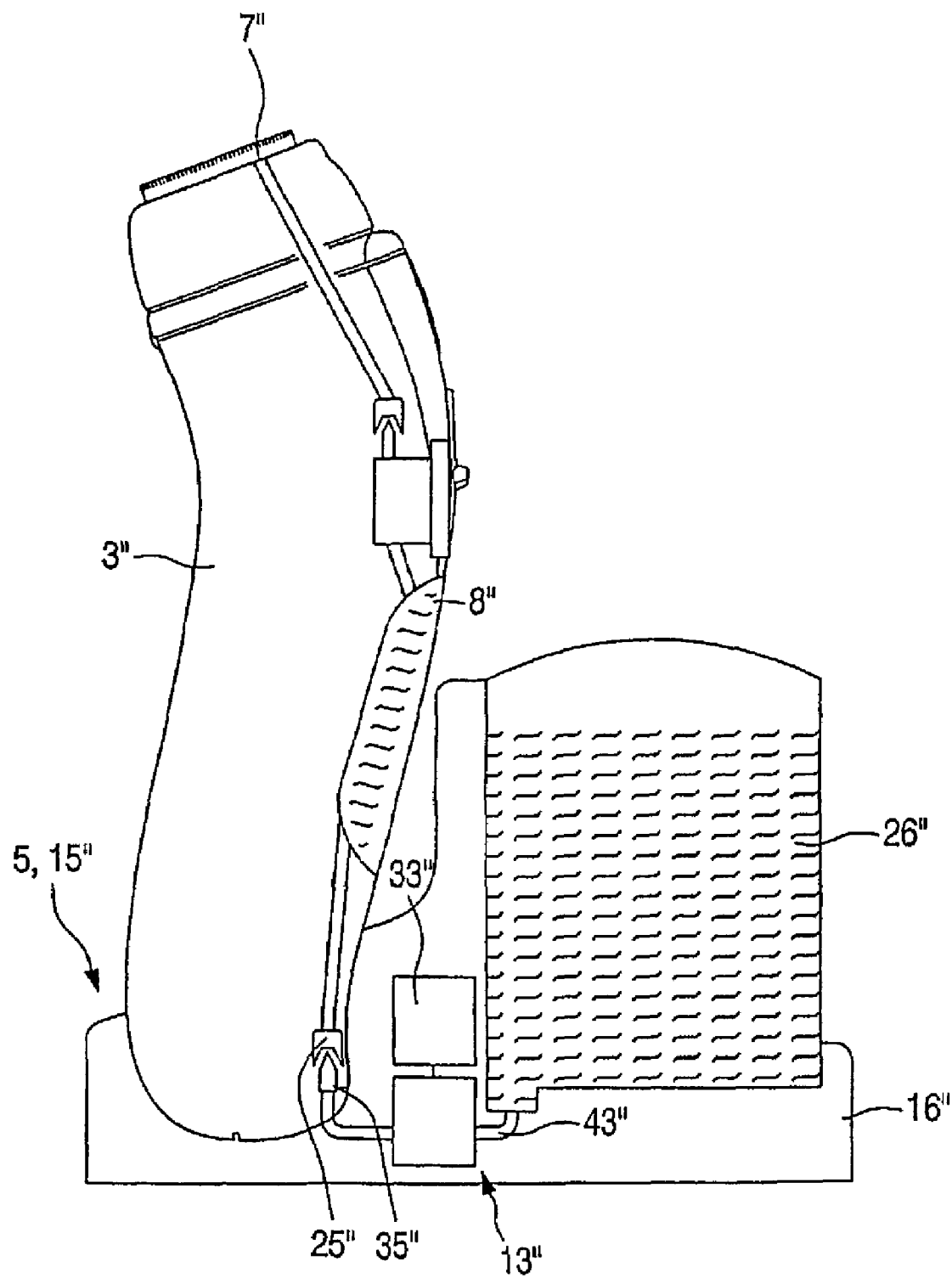

The invention will be described in more detail hereinafter with reference to the drawings, in which FIG. 1 shows a side view of a first embodiment of a personal care system comprising a personal care appliance according to the invention, FIG. 2 shows a top view of a second embodiment of a personal care system comprising a personal care appliance according to the invention, FIG. 3*a* shows a detail of the embodiment which is shown in FIG. 2, and FIG. 3*b* shows a detail of a third embodiment of a personal care system comprising a personal care appliance according to the invention, and FIG. 4 shows a side view of a fourth embodiment of a personal care system comprising a personal care appliance according to the invention.

FIG. 1 shows a first embodiment of a personal care system 1 comprising a personal care appliance 2 according to the invention. In this embodiment the personal care appliance 2 is a toothbrush 21. This toothbrush 21 comprises a body 3, an additive outlet 7, and a first reservoir 8. During operation additive is transported from the reservoir 8 to the additive outlet 7, and applied to the teeth of a user. It is noted that the toothbrush may be a non-electrical toothbrush or a power toothbrush, and that transport of the additive to the additive outlet 7 may be manually driven, e.g. by a pumping action of the user, or electrically driven. The reservoir 8 is connected with said additive outlet 7 and has a refill inlet 25 for refilling said reservoir 8. The system 1 further comprises a refill unit 16 comprising a refill outlet 35 which can be coupled to the refill inlet 25 of the toothbrush 21 for refilling its reservoir 8. Said refill unit 16 comprises a second reservoir 26 and means 13 for transporting additive from the second reservoir 26 to the first reservoir 8, when the toothbrush 21 is coupled to the refill unit 16.

As can be seen in the Figure, the refill unit 16 is provided in a holder 5 for storing the personal care appliance 2 when it is not in use. The functions of storing and refilling of the toothbrush 21 are integrated into the holder 5, by means of which the period of inactivity of the toothbrush 21 during storage may be utilized for refilling the reservoir 8 of the toothbrush 21. The system 1 thus also does not need separate components for the storage function and the refill function, which renders a relatively compact and simple system. This enhances the user-friendliness of the system.

FIG. 2 shows a second embodiment of a system according to the invention, in which the toothbrush 21 is a rechargeable power toothbrush and the holder 5 comprises a charging device 15 for charging the toothbrush 21 when stored in the holder 5. In this manner storage, refilling and recharging of the toothbrush are integrated within one holder. The period of inactivity of the toothbrush 21 during storage may be utilized for refilling and for recharging of the toothbrush 21, and the system comprises only one component, the holder 5, for realizing these three functions. In this embodiment the charging device 15 comprises inductive coils 61, but it is noted that any other known type of charging device may be used, depending on the type of rechargeable electrical personal care appliance comprised in the system. The system furthermore comprises power supply means 60 of a type which is known per se, and which are shown schematically here.

As furthermore can be seen in FIG. 2, the system in this embodiment comprises a sensor 14 for automatic activation of the means 13 for transporting additive on placing of the personal care appliance 2 in the holder 5'. The sensor 14 detects the presence of the toothbrush 21 in the holder 5' and provides a signal to a processing unit 33 which activates the transporting means 13' in response to said signal. In this manner the user only has to perform one simple operation, placing the toothbrush into the holder, to realize both storage of the toothbrush and activation of refilling of the reservoir of the toothbrush. The system thus offers a way of refilling the reservoir of the toothbrush which is comfortable for the user. It is noted that the sensor may comprise for example an optical sensor, but may also comprise any other known type of sensor which is capable of detecting the presence of the appliance in the holder.

When the transporting means are activated automatically, it is desirable for safety reasons that they are also de-activated automatically, when the reservoir of the toothbrush is full. The means 13' for transporting additive comprise a transport channel 43 between the second reservoir 26' and the refill outlet 35', via which the additive is transported to the reservoir of the toothbrush. At a certain moment the reservoir of the personal care appliance will be full and an overpressure will occur in the transport channel 43. The system comprises a pressure sensor 50 which detects the overpressure in said transport channel 43 and provides a signal to the processing unit 33 which de-activates the transporting means 13 in response to said signal. In this manner a reliable protection against overpressure within the system is offered, and no user intervention is necessary.

In this embodiment the pressure sensor 50 comprises a switch 51, which co-operates with a flexible membrane 52 which is provided in a wall 44 of the transport channel 43, as can be seen in FIG. 3*a* in more detail in a side view of the transport channel 43. When the overpressure in the transport channel occurs, the flexible membrane 52 curves outwardly under the influence of said overpressure and contacts the switch 51. The switch then sends the signal to the processing unit 33 to de-activate the transporting means 13'. The membrane can be manufactured in an easy and cost-effective manner, and the switch can be kept relatively simple, since it does not come into contact with any additive. In this manner a reliable and cost-effective construction for a pressure sensor is realized. In another embodiment as shown in FIG. 3*b*, a part of the transport channel 43 is formed by the flexible membrane 52'. This membrane also co-operates with a switch as described before. This also offers a cost-effective construction of the pressure sensor, since the membrane may be injection moulded together with the transport channel 43.

Furthermore, a distance between the switch 51 and the membrane 52 is adjustable for adjusting a value of a pressure at which the flexible membrane 52 contacts the switch 51. The pressure at which the membrane is to curve and contact the switch and deactivate the transporting means may differ among the various types of personal care appliances that may be comprised in the system. The system may furthermore also comprise more than one personal care appliance which may be refilled in the holder. When the distance between the switch and the membrane is adjustable, the same components can be used for the manufacture of for example a system which comprise a toothbrush and a system which comprises a shaver, or a system comprising two toothbrushes.

FIG. 4 shows a fourth embodiment of a personal care system according to the invention in which the personal care appliance is a shaver 22, which comprises a body 3", an additive outlet 7, and a first reservoir 8" which is connected with said additive outlet 7" and has a refill inlet 25" for refilling said reservoir 8". It is noted that next to toothbrushes and shavers, a system according to the invention may also comprise other personal care devices which are provided with a reservoir, such as for example a depilating device or a massaging device. The additives used with the system may comprise for example toothpaste, gel, lotion or cream, but also other known types of additives, depending on the type of personal care appliance.

It is furthermore noted that the personal care appliance may comprise more than one reservoir, such as for example a toothbrush with a reservoir for toothpaste, and a reservoir for a refreshing additive, which additives are applied sequentially to the teeth during operation. The refill unit in this situation also comprises two reservoirs for containing said two additives.

The invention claimed is:

1. A personal care system comprising:
a personal care appliance which comprises a body, an additive outlet, and a first reservoir which is connected with said additive outlet and has a refill inlet for refilling said reservoir;
a refill unit comprising a refill outlet which can be coupled to the refill inlet of the personal care appliance for refilling the first reservoir, the refill unit comprising a second reservoir and means for transporting additive from the second reservoir to the first reservoir, when the personal care appliance is coupled to the refill unit wherein the refill unit is provided in a holder for storing the personal care appliance when it is not in use,
the personal care appliance being rechargeable electrical personal care appliance and the holder comprising a charging device for charging the personal care appliance when the personal care appliance is stored in the holder.

2. A personal care system comprising:
a personal care appliance which comprises a body, an additive outlet, and a first reservoir which is connected with said additive outlet and has a refill inlet for refilling said reservoir;
a refill unit comprising a refill outlet which can be coupled to the refill inlet of the personal care appliance for refilling the first reservoir, the refill unit comprising a second reservoir and means for transporting additive from the second reservoir to the first reservoir, when the personal care appliance is coupled to the refill unit wherein the refill unit is provided in a holder for storing the personal care appliance when the personal care appliance is not in use
the personal care system comprising a sensor for automatic activation of the means for transporting additive on placing of the personal care appliance in the holder, by detecting presence of the personal care appliance in the holder and providing a signal to a processing unit which activates the transporting means in response to said signal.

3. A personal care system as claimed in claim 2, wherein the means for transporting additive comprise a transport channel between the second reservoir and the refill outlet and the system further comprises a pressure sensor for detecting an overpressure in said transport channel and for providing a signal to the processing unit which de-activates the transporting means in response to said signal.

4. A personal care system as claimed in claim 3, wherein the pressure sensor comprises a switch which co-operates with a flexible membrane which is provided in at least a part of a wall of the transport channel.

5. A personal care system as claimed in claim 4, wherein a part of the transport channel is formed by the flexible membrane.

6. A personal care system as claimed in claim 4, wherein a distance between the switch and the membrane is adjustable for adjusting a value of a pressure at which the flexible membrane contacts the switch.

7. A personal care system as claimed in claim 2, wherein the personal care appliance is a tootbrush.

8. A personal care system as claimed in claim 2 wherein the personal care appliance is a shaver.

9. A personal care system comprising:
a personal care appliance which comprises a body, an additive outlet and a first reservoir connected to the additive outlet, the first reservoir having a refill inlet; and
a refill unit comprising a refill outlet capable of being coupled to the refill inlet, a second reservoir, a transport channel extending, when the personal care appliance is coupled to the refill unit, from the second reservoir to the first reservoir, and a pump unit capable of maintaining pressure of additive in the transport channel,
the transport channel being provided with a pressure sensor comprising a switch and with a flexible membrane in at least a part of a wall of the transport channel,
the switch co-operating with the membrane to provide a signal to a processing unit,
the processing unit being configured to de-activate the pump unit, in response to said signal.

10. A personal care system as claimed in claim 9, wherein the personal care appliance is a toothbrush.

11. A personal care system as claimed in claim 9, wherein the personal care appliance is a shaver.

* * * * *